(12) United States Patent
Kessler et al.

(10) Patent No.: US 8,794,072 B2
(45) Date of Patent: Aug. 5, 2014

(54) SCANNING ACOUSTIC MICROSCOPE WITH PROFILOMETER FUNCTION

(75) Inventors: Lawrence W. Kessler, Buffalo Grove, IL (US); Michael G. Oravecz, Lombard, IL (US); Zhiqi Guo, Palatine, IL (US)

(73) Assignee: Sonoscan, Inc., Elk Grove Village, IL (US)

( * ) Notice: Subject to any disclaimer, the term of this patent is extended or adjusted under 35 U.S.C. 154(b) by 697 days.

(21) Appl. No.: 12/244,460

(22) Filed: Oct. 2, 2008

(65) Prior Publication Data

US 2009/0095086 A1 Apr. 16, 2009

Related U.S. Application Data

(60) Provisional application No. 60/979,021, filed on Oct. 10, 2007, provisional application No. 61/038,460, filed on Mar. 21, 2008.

(51) Int. Cl.
*G01N 29/06* (2006.01)

(52) U.S. Cl.
USPC .............................................. 73/634; 73/633

(58) Field of Classification Search
USPC .................................................... 73/633, 634
See application file for complete search history.

(56) References Cited

U.S. PATENT DOCUMENTS

| 2,937,522 | A | * | 5/1960 | McGaughey | 73/633 |
| 3,792,613 | A | * | 2/1974 | Couture | 73/629 |
| 4,021,771 | A | * | 5/1977 | Collins et al. | 367/8 |
| 4,455,872 | A | * | 6/1984 | Kossoff et al. | 73/618 |
| 4,503,708 | A | * | 3/1985 | Kino et al. | 73/628 |
| 4,513,384 | A | * | 4/1985 | Rosencwaig | 702/170 |
| 4,768,155 | A | * | 8/1988 | Takishita et al. | 702/39 |
| 4,781,067 | A | * | 11/1988 | Cichanski | 73/620 |
| 5,029,476 | A | * | 7/1991 | Metala et al. | 73/620 |
| 5,241,287 | A | * | 8/1993 | Jen | 333/143 |
| 5,331,855 | A | * | 7/1994 | Takashita et al. | 73/602 |
| 5,475,613 | A | * | 12/1995 | Itoga et al. | 702/39 |
| 5,602,336 | A | * | 2/1997 | Takeuchi et al. | 73/624 |
| 5,641,706 | A | * | 6/1997 | Tjaden et al. | 438/20 |
| 6,880,387 | B2 | * | 4/2005 | Kessler et al. | 73/105 |
| 6,890,302 | B2 | * | 5/2005 | Oravecz et al. | 600/443 |
| 6,981,417 | B1 | * | 1/2006 | Oravecz | 73/619 |
| 7,132,617 | B2 | * | 11/2006 | Lee et al. | 219/109 |
| 2003/0089171 | A1 | * | 5/2003 | Kenefick et al. | 73/597 |
| 2007/0180914 | A1 | * | 8/2007 | Kessler | 73/607 |

OTHER PUBLICATIONS

DiStefano et al., "Acoustic Contour Mapping", IBM Technical Disclosure Bulletin, vol. 25, Issue 10, pp. 5103-5108, Mar. 1983.*

* cited by examiner

*Primary Examiner* — Peter Macchiarolo
*Assistant Examiner* — Rose M Miller
(74) *Attorney, Agent, or Firm* — McCracken & Frank LLC

(57) ABSTRACT

A scanning acoustic microscope, includes an ultrasonic transducer, a data storage memory, a display, a scanner assembly, and a controller. The controller is adapted to cause the motor to move the transducer along a path with respect to a sample, and cause the ultrasonic transducer to emit a pulse of acoustic energy towards the sample at each point in a plurality of points along the path. In addition, the controller is adapted to cause the ultrasonic transducer to receive a set of reflection signals that correspond to each of the pulses emitted therefrom. The sets of reflection signals are used to generate an image of a profile of the sample and an image representative of acoustic impedance features in the interior of the sample. The image of the profile of the sample shows a variation in height across a surface of the sample.

22 Claims, 18 Drawing Sheets

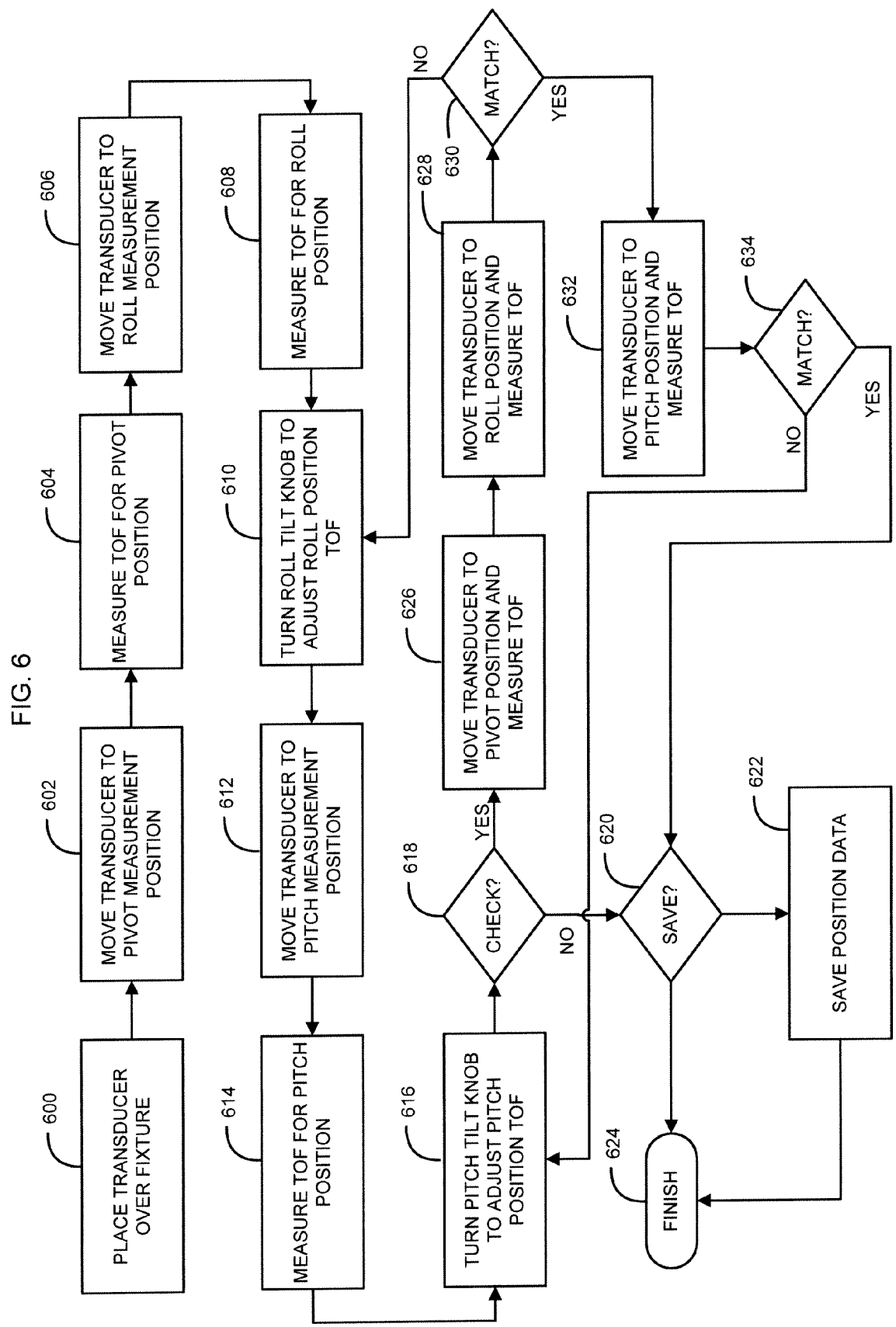

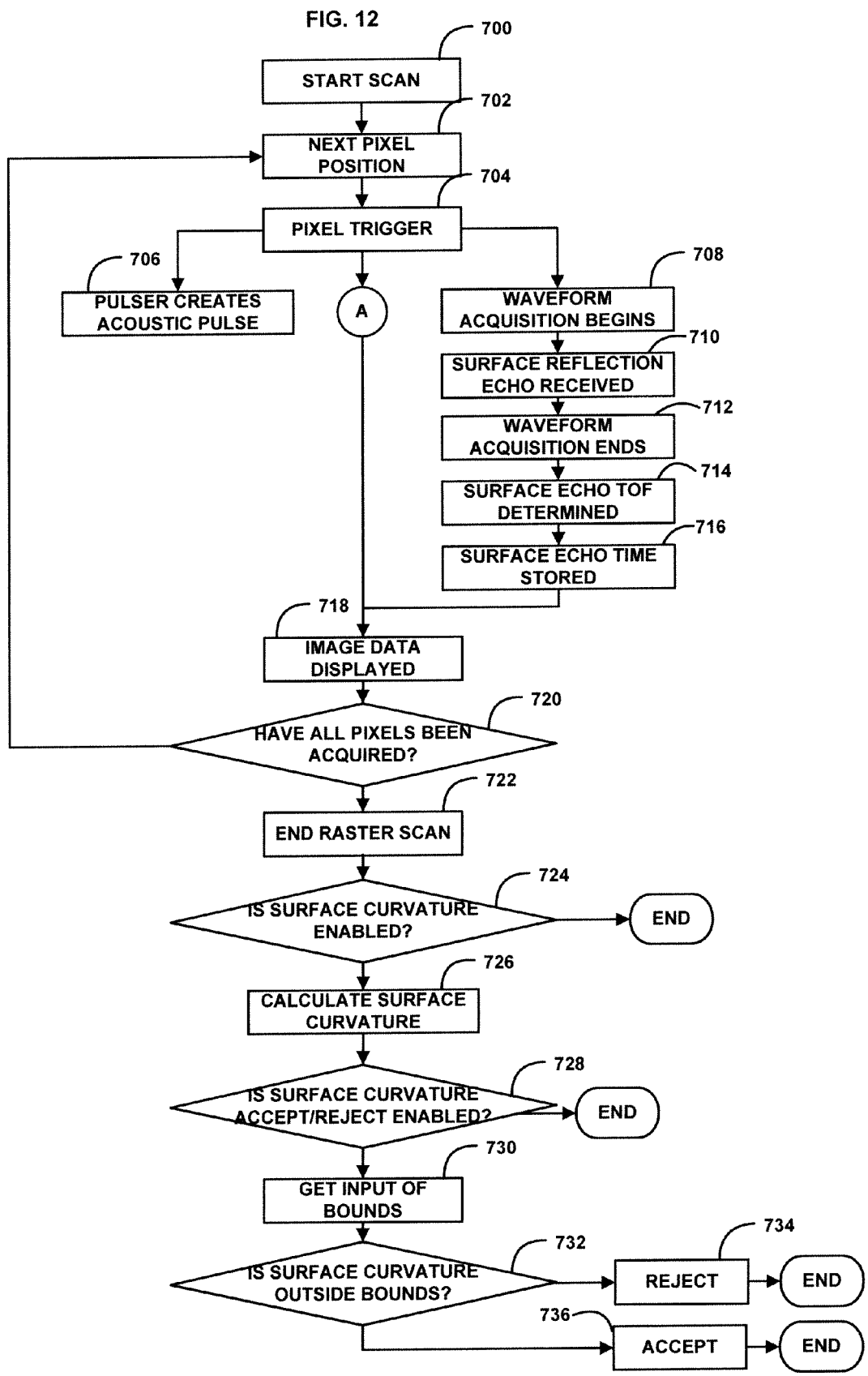

SCANNING ACOUSTIC MICROSCOPE WITH PROFILOMETER FUNCTION

CROSS-REFERENCE TO RELATED APPLICATION

The content of U.S. provisional application Ser. No. 60/979,021, filed Oct. 10, 2007 and 61/038,460, filed Mar. 21, 2008 is incorporated by reference into this application as if fully set forth herein. The following US patents and applications are assigned to Sonoscan, and generally relate to various aspects of scanning acoustic microscopy: U.S. Pat. Nos. 4,518,992, 4,781,067, 4,866,986, 5,351,544, 5,684,252, 6,357,136, 6,460,414, 6,880,387, 6,890,302, 6,895,820, 6,981,417, and 7,000,475, as well as Ser. No. 11/626,177 filed Jan. 23, 2007. All such patents and applications are incorporated by reference as if fully set forth herein.

DESCRIPTION OF RELATED ART

As is well known in the art a scanning acoustic microscope typically comprises a transducer which is driven by voltage pulses which may have amplitudes of, for example, 100 volts or more and are typically in the frequency range of tens of megahertz to 100 megahertz or higher.

The pulsed acoustic beam penetrates the target, which may be an IC package, for example. A fraction of the energy passes through the target, and the remainder is absorbed, scattered, or reflected. In many applications sufficient energy is returned to the transducer (after a delay) to be sensed. Acoustic energy is almost totally reflected by an air gap. Thus acoustic microscopes have proven to be extremely useful in locating disbonds (air gaps) between internal layers of a device such as an IC package.

The return signal is an echo composed of a range of frequencies centered around the transducer's resonant frequency. As described further in U.S. Pat. No. 6,981,417, the return signal is commonly known as the "A" waveform or "A-scan", and in practice contains a great deal of information about acoustic impedance perturbations or features in the body of the IC package.

As is well known in the art, a time domain signal received by the acoustic microscope during a scanning session is conventionally gated by a gating process. During the gating process, a gate isolates a pixel-representative signal segment associated with a single pixel.

Gating of the signal permits a user to examine any chosen level in the target simply by selecting an appropriate delay time for the gate. For example, a single pixel segment might be captured with a gate 100 nanoseconds wide set at a delay of 384-484 nanoseconds. If a deeper level were to be visualized, a longer delay would be employed.

SUMMARY OF THE DISCLOSURE

In accordance with the invention, there is provided a scanning acoustic microscope capable of collecting and displaying any profile image of a sample including a surface profile, an internal profile or any combination of the two.

In accordance with another aspect of the invention, the scanning acoustic microscope may also be capable of simultaneously collecting and displaying an internal acoustic image of a sample.

In accordance with yet another aspect of the invention, the scanning acoustic microscope may be configured to simultaneously display a surface profile, a time domain signal representation, a frequency domain signal representation, or any representation of features on or within a sample.

BRIEF DESCRIPTION OF THE DRAWINGS

FIG. 6 is a flowchart showing the steps of manually adjusting a tilt fixture.

FIG. 12 is a flowchart that shows program steps that are followed to allow a scanning acoustic microscope to collect acoustic profile information.

DETAILED DESCRIPTION

Figure 1:
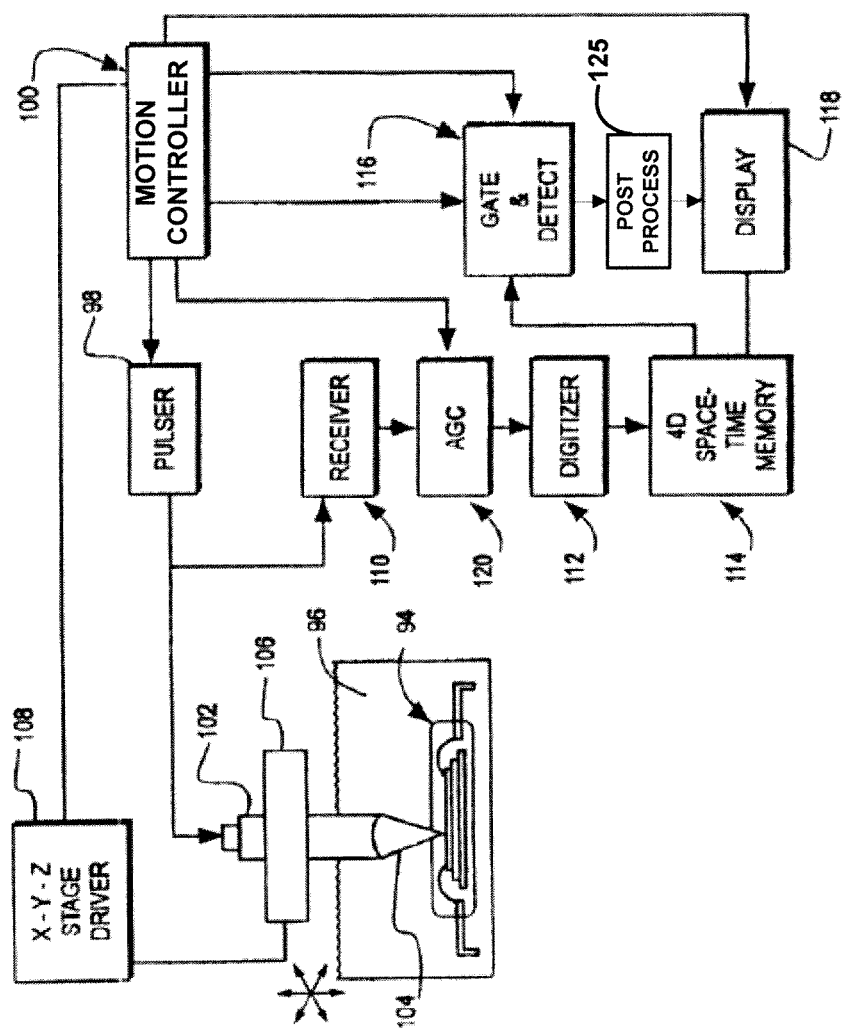
FIG. 1 is a schematic illustration of an acoustic imaging microscope.

FIG. 1 illustrates in highly schematic form an acoustic imaging microscope, shown as being adapted to inspect a sample, for example, an integrated circuit ("IC") package 94 submerged in a coupling medium 96. Although an IC is used in the example, the sample may be any of a variety of tangible objects and is not restricted to an IC. A sample may be, for example, a ceramic plate, a diamond, a medical device, a machine plate, or an electrical component such as a capacitor or a transistor. A pulser 98, under the control of a motion controller 100 excites a transducer 102 to generate a pulsed ultrasonic probe 104, typically at frequencies ranging from 10 MHz or lower to 230 MHz or higher. The transducer 102 is scanned in X, Y, and Z coordinates by an X-Y-Z stage 106 through an X-Y-Z stage driver 108 under the control of motion controller 100.

Acoustic reflections from impedance features in the IC package 94 are sensed by a receiver 110. Acoustic reflectance signals developed by receiver 110 may be in analog form. The analog acoustic reflectance signals developed by receiver 110 are supplied to an automatic or computer-driven gain control ("AGC") circuit 120. The AGC circuit 120 may sometimes be employed to adjust the retrieved acoustic reflectance signal to correct or reduce signal amplitude errors such as may be caused by acoustic energy absorption by the examined sample. The output of the AGC 120 is supplied to a digitizer 112 where the analog signals are quantized, for example by a 2 GHz analog-to-digital converter, into digital bytes for storage in a 4D space-time memory 114.

As explained in U.S. Pat. No. 6,981,417, the 4D space-time memory 114 is of a type adapted to store time-space data corresponding to three spatial dimensions, and associated with each point in 3D space, a set of data corresponding to A-scans associated with each point in space. In accordance with the present invention, for each point in a 3D volume, a sequence of data bytes are stored. The data bytes describe the time-dependent amplitude fluctuations of an acoustic reflectance signal returned upon interrogation of a particular point in sample space. The length of the stored acoustic reflectance signal is a function of the width of a capture gate that is set by the operator or generated by a program or algorithm.

As will become evident from a more detailed description to follow, to create a display, the stored space-time data stored within memory 114 is, in one method, gated and peak detected in a gate and detect component 116 which may be a software algorithm or hardware signal processor. A conventional peak-detected output signal from component 116 is processed in a post processor 125. The post processor 125 comprises an aspect of the present invention and will be described at length below.

After being processed in post processor 125, the acquired data signals are employed to modulate a display 118, which may be CRT monitor, for example. Alternatively, as is well known, time-of-flight data may also be displayed.

Figure 2:
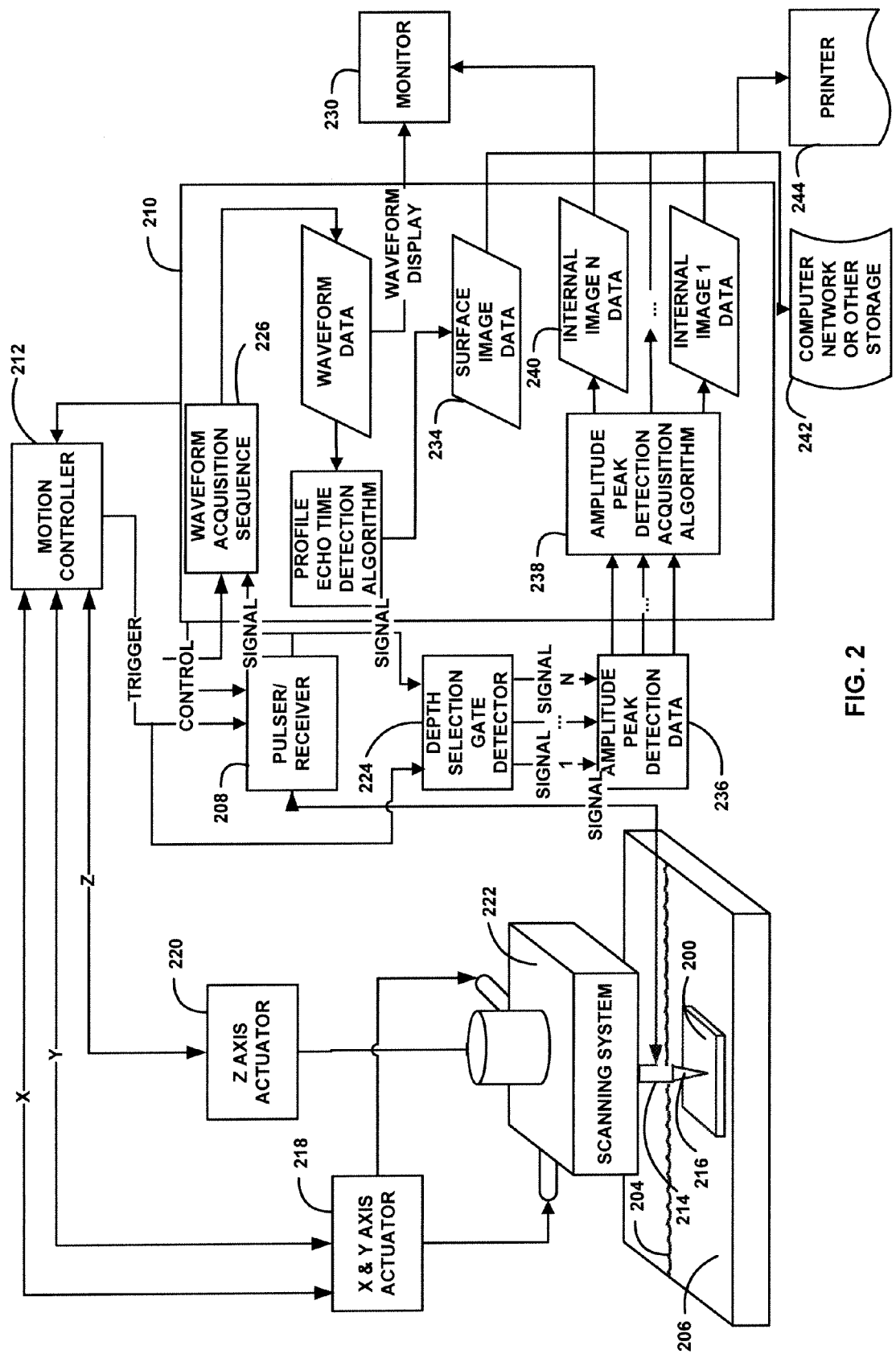
FIG. 2 is a schematic illustration of an alternative acoustic imaging microscope.

A second embodiment of a scanning acoustic microscope is shown in FIG. 2. FIG. 2 illustrates a schematic form of an acoustic imaging microscope implementing the principles of the invention. Similar to FIG. 1, the acoustic imaging microscope of FIG. 2 is shown as being adapted to inspect an IC 200 submerged in a coupling medium 204 in a tank 206. A pulser/receiver 208 under the control of a host computer 210 upon receiving a trigger from a motion controller 212, excites a transducer 214 to generate a pulsed ultrasonic probe 216. The transducer 214 is scanned in the X and Y axis using an X and Y axis actuator, and in the Z axis using a Z axis actuator 220 through the scanning system 222 under the control of motion controller 212

The motion controller 212, during an image scanning mode, upon moving the actuators 218, 220 to a location to be scanned, provides a trigger to the host computer 210 and a depth selection gate detector 224. Within the host computer 210, upon receiving a trigger from motion controller 212 a waveform acquisition sequence 226 begins and waits for an analog acoustic reflectance signal developed by the pulser/receiver 208. Similarly, depth selection gate detector 224 upon receiving a trigger from motion controller 212 begins an amplitude peak acquisition sequence.

Acoustic reflections from impedance features in the IC 200 are sensed by the pulser/receiver 208. Acoustic reflectance signals developed by the pulser/receiver 208 may be in analog form. The analog acoustic reflectance signals developed by the pulser/receiver 208 are supplied to the depth selection gate detector 224 and the host computer 210. Waveform data 228 is collected by the host computer 210 during the waveform acquisition sequence 226 and may be displayed on monitors 230. Waveform data 228 is processed using a surface profile echo detection algorithm 232 and surface profile image data 234 may be displayed on monitors 230.

A user may choose to detect internal images at multiple depths within a sample. Depth selection gate controller 224, upon receiving the acoustic reflection signals may develop a plurality of signals corresponding to each depth selection gate selected by the user. Amplitude peak detection data 236 is processed using an amplitude peak acquisition algorithm 238 and internal image data 240 corresponding to each depth selection gate selected by the user may be displayed on monitors 230. All surface and internal image data may be stored on a computer network or in internal memory 242 and/or sent to a printer 244 coupled to the host computer 210.

Figure 3A:
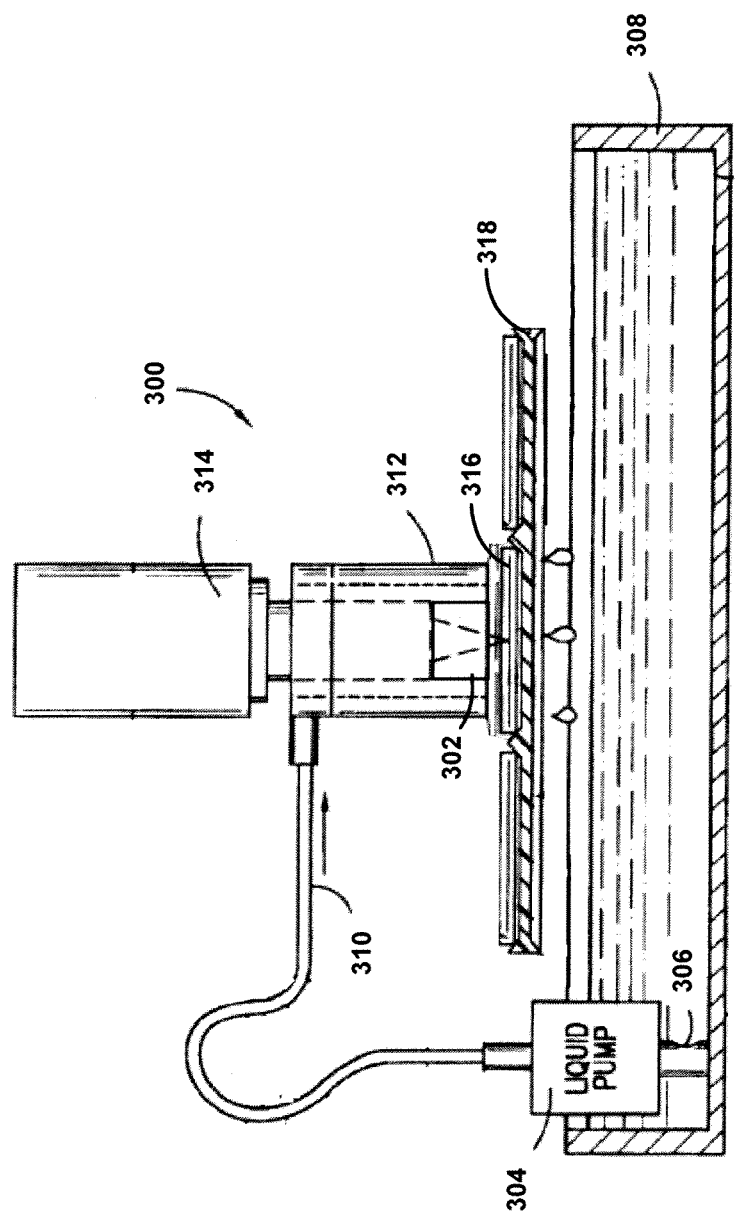
FIGS. 3A and 3B illustrates alternative transducer assemblies which may be implemented in certain applications of the present invention.

FIG. 3A illustrates an alternative to the transducer shown in FIG. 1. FIG. 3A illustrates a "waterfall" transducer 300 wherein pulses of ultrasonic energy are emitted through a flow of coupling fluid 302. The "waterfall" transducer, as illustrated may be useful when scanning a circuit board that may include both waterproof parts and parts susceptible to damage if it came in contact with the fluid 302. The transducer 300 may be positioned above only those parts that are waterproof, thus, protecting the non-waterproof parts. A liquid pump 304 having an inlet 306 is shown positioned within the liquid coupling medium 302 in a tank 308. The outlet of the liquid pump 304 is connected by flexible conduit 310 to a housing 312 of transducer 314. The flow of fluid 302 will only contact the selected portion of the part 316. A tray 318 is adapted to hold the part 318 above the tank 308. As illustrated, the coupling fluid 302 is collected in the tank 308 and may be recirculated through the inlet 306.

Figure 3B:
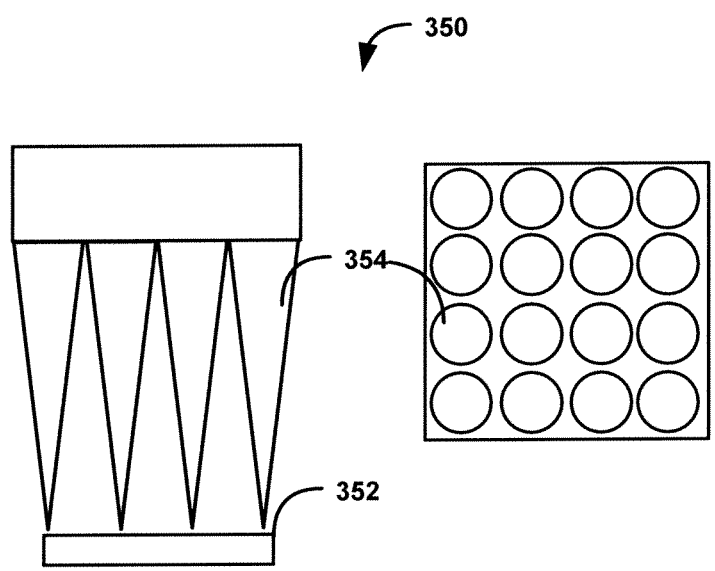

In another alternative, the transducer system of FIG. 1-FIG. 3A may be implemented using a transducer array 350 as illustrated in FIG. 3B. The term "the system" as referenced herein will refer to the transducer system of FIG. 1-3A. Where the transducers of FIG. 1-FIG. 3A must physically move to scan each point of a part, the transducer array 350 may be used to minimize or completely eliminate any physical movement of the transducer while scanning a part. The array 350 may be positioned over a part 352. The beams 354 may simultaneously scan the part 352 greatly reducing the scanning time. If the area of the part 352 is greater than the area of the array 350, the array 350 may be configured to move to the next position and scan the rest of the part 352. Although the configuration shown is a square array of transducers, other configurations may be used such as a linear, rectangular, triangular, circular, or semi-circular array.

Figure 4A:
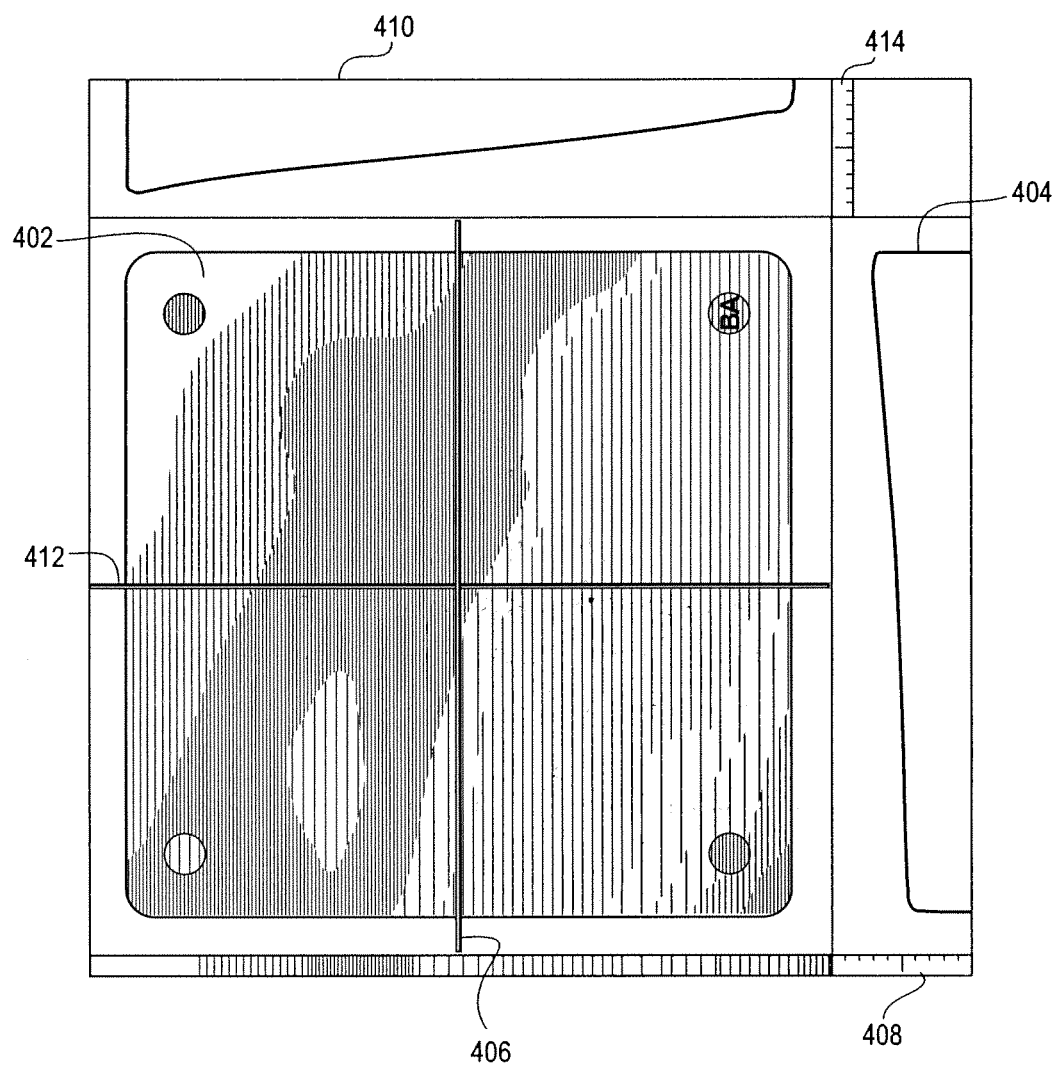
FIG. 4A is an illustration of a profile scan of an integrated chip useful in understanding an aspect of the present invention.

In accordance with an exemplary embodiment of the invention, acoustic surface data is collected and then displayed as a color-coded image in which each color corresponds to a topographical distance measurement as, for example, shown in FIG. 4A. The sensitivity of the acoustic software module is in the micron range, and is not dependant upon the surface smoothness, color or optical characteristics. FIG. 4A shows a profile image of an integrated chip (IC) 402. A graph 404 along the Y axis of FIG. 4A shows the variation of height across the surface of the IC 402 along a vertical line 406. A ruler 408 may be imposed on the graph 404 to give an indication of the height along the vertical line 406 referenced to a zero point. Similarly, a graph 410 along the X axis of FIG. 4A shows the variation of height across the surface of the IC 402 along a horizontal line 412. Similar to the ruler 408, a ruler 414 may be imposed on the graph 410 to give an indication of the height along the horizontal line 412 as referenced to a zero point. Of course, the graphs of the profile image are not limited to the vertical and horizontal lines. The graphs may be a collection of data between other points such as a diagonal line from one corner of the IC 402 to another corner of the IC 402, a curved line, or a user modifiable line.

Figure 4B:
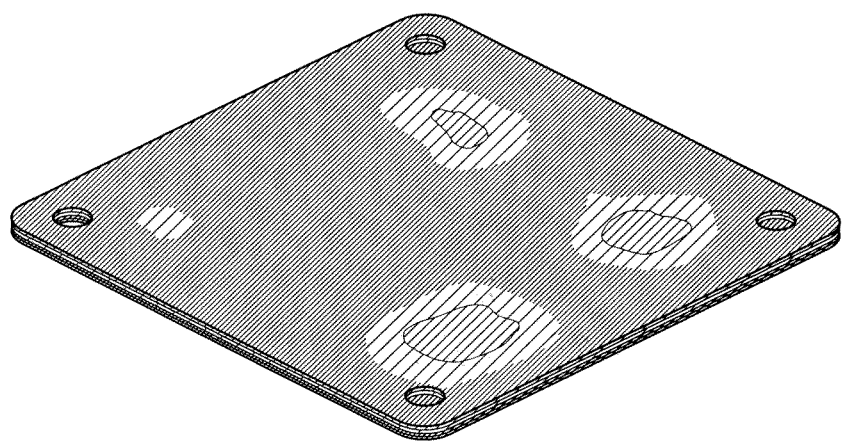
FIG. 4B is a 3-dimensional illustration of an integrated chip.

The acoustic surface data collected may also be used to generate a 3-dimensional image of the IC 402 as shown, for example, in FIG. 4B. Using mathematical and graphical rendering programs such as MATLAB, the acoustic surface data may be transformed and projected as a 3-D image as shown in FIG. 4B.

Figure 5A:
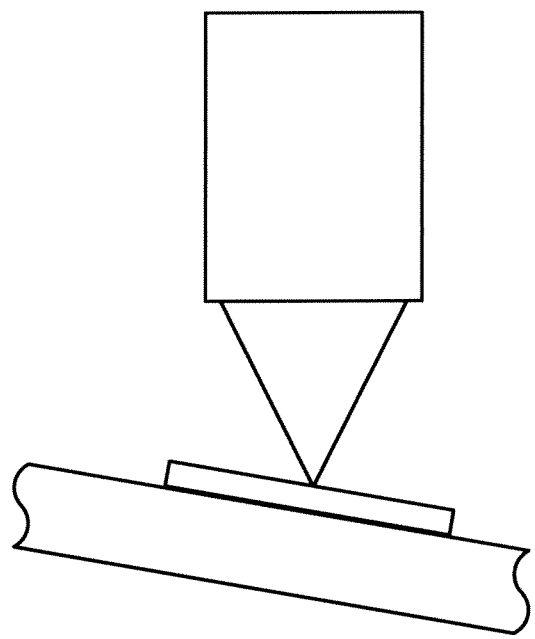
FIG. 5A illustrates a side view of an ultrasonic pulse that is directed towards a tilted part.

External factors may induce errors to the acoustic surface data. Factors such as unevenness of the floor on which the machine stands, or the table on which the tank sits may cause a "tilting" of the image as shown in FIG. 5A. One aspect of the present invention concerns the use of a universal tilting fixture that allows 2-axis orthogonal tilt adjustments to be made with, for example, a matching tank. This utility assists the user in removing tilt from the part being scanned. For general scanning and especially for surface flatness inspection and main bang imaging, the best data is obtained when the part surface is parallel to the scanner. The gating setup for surface flatness inspection and main bang imaging is greatly simplified when the part is parallel to the scanner. The tilt of the tilting fixture can be adjusted with two orthogonal tilt adjustments (e.g. Roll and Pitch) and a fixed pivot.

Figure 5B:
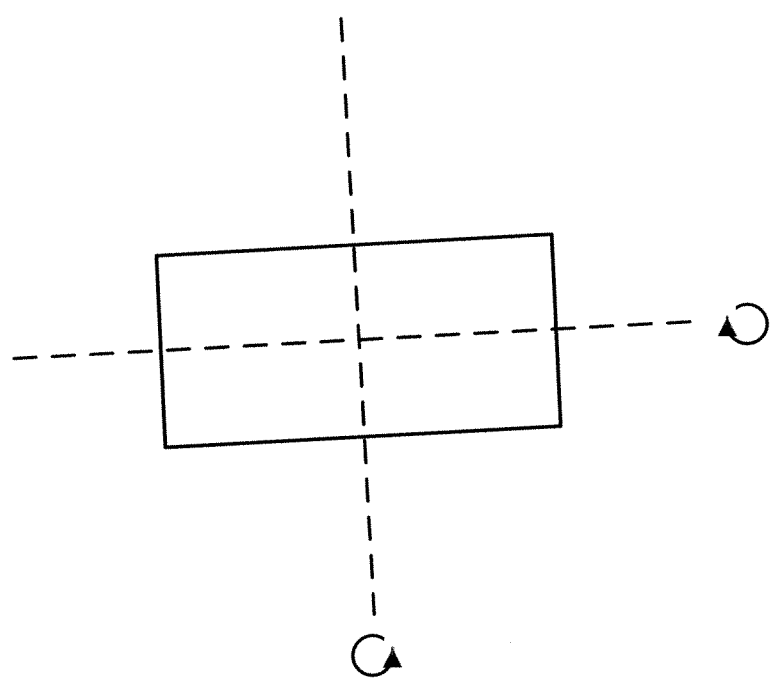
FIG. 5B is a schematic diagram showing how an exemplary tilt fixture can be rotated about two different axes.
Figure 5C:
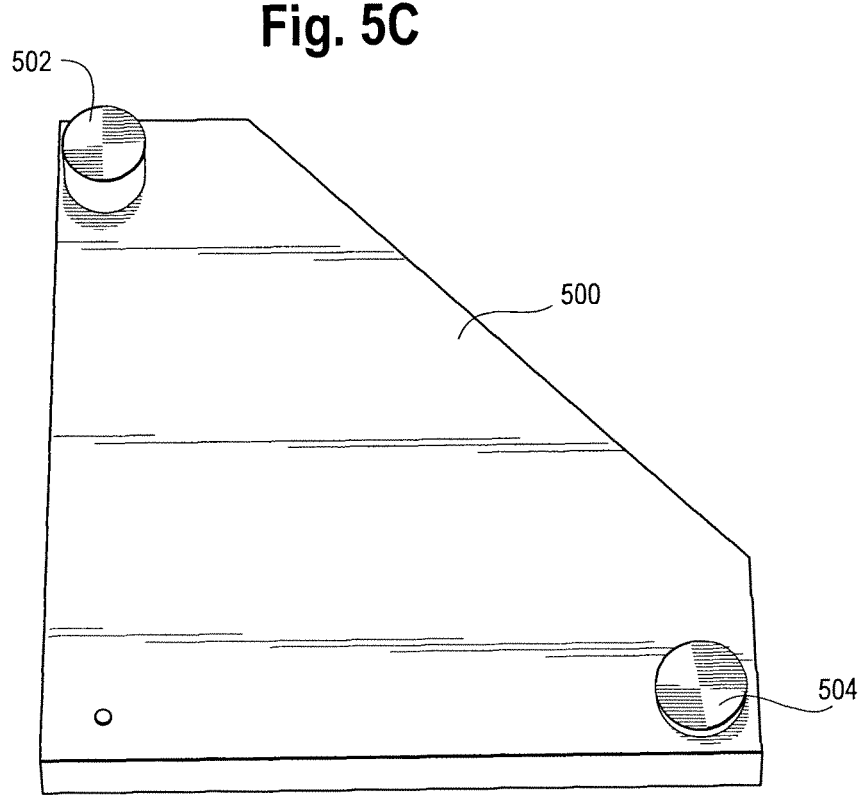
FIG. 5C is an annotated perspective view of an exemplary tilt fixture shown with exemplary roll and pitch axes.

FIG. 5B is a schematic diagram showing how an exemplary tilt fixture can be rotated about two different axes. Referring to FIG. 5C, an annotated perspective view of an exemplary tilt fixture 500 is shown with exemplary roll and pitch axes. The tilt fixture 500 includes thumbscrews 502, 504 that are used to raise and lower each corner of the fixture 500. On the top of the fixture is a knurled knob for rotating the screw by hand. Underneath the tilt fixture is a ball end screw tip (not shown) that rests on the tank bottom (with kinematic coupling).

Regarding the shape of the tilt fixture, the exact shape can change. The illustrated design of FIG. 5C keeps the center of gravity close to the fixed ball in the corner of the fixture so there is no need to use springs. By removing the corner away from the from the fixed ball, the center of gravity moves to a stable position between the three balls. If a rectangular fixture is used, a spring or other means of providing stability may be utilized.

FIG. 6 is a flowchart showing the steps to manually adjust the tilt fixture shown in FIG. 5C. At step 600 the transducer is placed over the 2-axis tilt fixture. The transducer then proceeds to the Pivot Measurement Position at step 602. In the case of the fixture 500 shown in FIG. 5C the Pivot Measurement Position will be located at the lower left corner. At step 604 an average TOF is measured. The average TOF may be used as a reference value to calibrate each corner of the fixture 500. At step 606 the transducer is moved to the Roll Measurement Position, the lower right corner of the fixture as referenced to FIG. 5C. An average TOF is measured for the Roll Measurement Position. The system compares the Roll Measurement Position TOF to the reference TOF measured in step 604. At step 610, based on the difference of the TOF measurement at step 604 and 608, the velocity of the coupling medium, and the pitch of the Roll tilt screw, the user may be told to rotate the Roll tilt knob x.x amount of turns clockwise or counterclockwise. For a more precise adjustment an indicator light may be displayed on the display screen. As the user is turning the knob, when the Roll TOF matches the Pivot Position TOF the indicator light may change colors, for example, from red to green. Of course, the indicator may also be a physical light on the device, or an audible indicator alerting the user when the positions are balanced.

Once the Roll TOF matches the Pivot Position TOF, at step 612, the transducer moves to the Pitch measurement position, the top left corner as referenced to FIG. 5C. At step 614, the average TOF is measured for the Pitch measurement position. Based on the difference of the TOF measurement at step 604 and 614, the velocity of the coupling medium, and the pitch of the Pitch tilt screw, at step 616, the user may be told to rotate the Roll tilt knob x.x turns clockwise or counterclockwise. An indicator light similar to the light described above may be used for a more precise adjustment. At step 618, the user may be prompted to check each of the positions again for accuracy of the adjustment. If a check is not chosen to be performed, at step 620, the user may be prompted to save the positions of the Pitch and Roll knobs for future reference. If the user decides to save the positions the system proceeds to step 622. If the user does not decide to save the positions then the manual tilt adjust is finished at step 624. If the user chooses to perform the check, at step 626, the transducer may proceed to the Pivot measurement position and measure the average TOF. The transducer may then proceed to the Roll measurement position at step 628 and measure the TOF of the Roll position. At step 630, the Pivot TOF is compared to the Roll TOF. If the TOFs do not match then the system will proceed back to step 610. If the TOFs do match then the transducer may proceed to the Pitch position and measure the TOF at step 632. The TOF at the Pitch position will be compared to the TOF at the Pivot position from step 626 at step 634. If the TOFs do not match the system will proceed back to step 616 where the Pitch position will be readjusted. If TOFs match then the system proceeds to step 620 where the steps of saving the positions are the same as described above.

The system may also be adapted to remove tilt from a part already placed on the fixture 500. To remove tilt from a part installed on the fixture 500 the steps are essentially the same as described above. Instead of placing the transducer at the corners of the fixture 500 the transducer may be placed at a corner of the part and the TOFs measured and compared and the fixture tilt adjusted accordingly.

Figure 7:
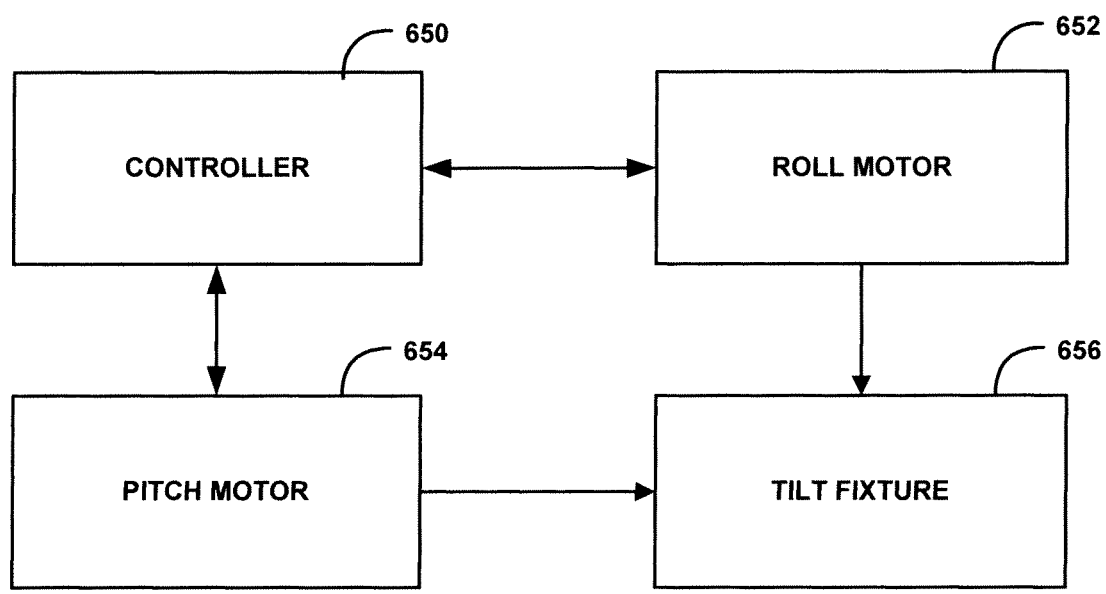
FIG. 7 is a schematic block diagram of a system that allows a scanning acoustic microscope to perform tilt adjustment measurements under automatic control.

The system of FIG. 5C may also be motorized to allow the tilt correction to be done automatically. FIG. 7 is a schematic block diagram of a system that allows a scanning acoustic microscope to perform tilt adjustment measurements under automatic control. A controller 650 is used to control a roll motor 652 and a pitch motor 654. The roll motor 702 and the pitch motor 704 are connected to a tilt fixture 656 to automatically adjust the tilt of the fixture. Instead of the user manually adjusting the knobs as described in steps 610 and 616 above, the Roll motor 652 and the Pitch motor 654 respectively, automatically adjust the tilt fixture 656 so the measured TOF matches the reference TOF.

Figure 8:
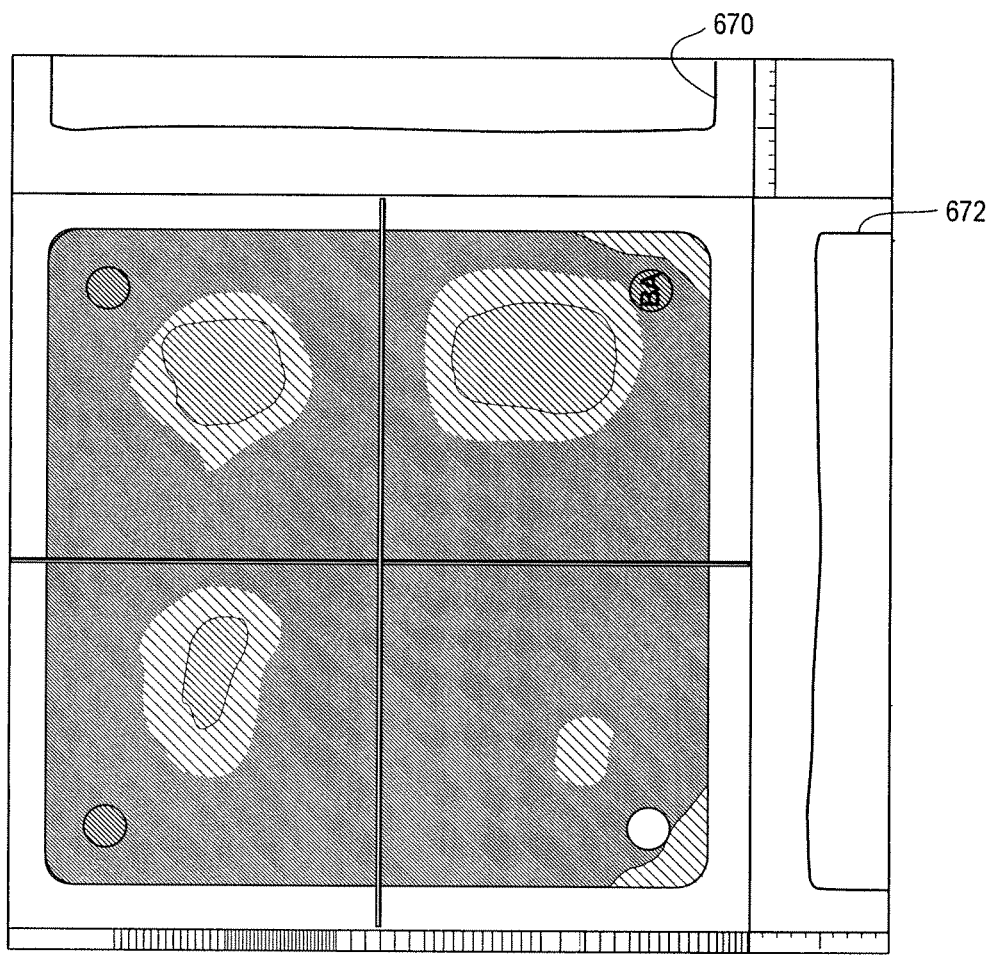
FIG. 8 is a normalized profile scan of the IC illustrated in FIG. 4A.

Physical correction of the tilt may, at times, be cumbersome and time consuming. Thus, one aspect of the invention may allow the user to "normalize" the data virtually adjusting for tilt after collecting the acoustic surface data. Referring back to FIG. 4A, the graphs 404 and 410 show substantial tilt to the right and the bottom of the IC 402. The user may choose to normalize the acoustic surface data in a variety of manners. One option may be to select three points on the profile image of the part, usually three corners of the part. An average of the three corners may be determined, and the image may be adjusted accordingly as shown in FIG. 8. As illustrated in FIG. 8, the end points on the graphs 670, 672 are now normalized compared to the end points of the graphs in FIG. 4A. Correspondingly, the color-coded image has also been changed due to the tilt adjustment giving a more precise profile height deviation image.

Figure 9:
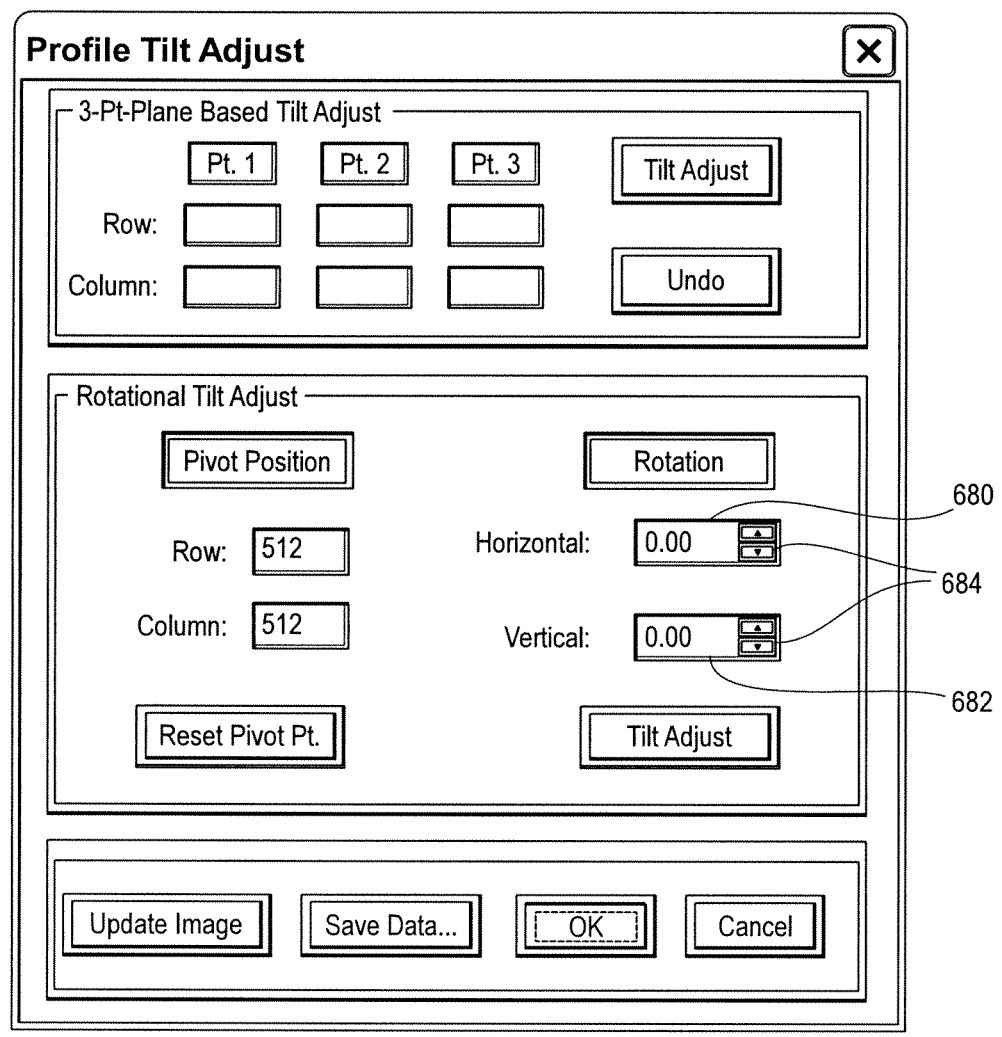
FIG. 9 is an illustration of a profile tilt adjust screen used to manually normalize a profile image.

A second option to normalize the acoustic surface data may be to use the Rotational Tilt Adjust from the Profile Tilt Adjust screen shown in FIG. 9. To manually normalize the data the user must first select a pivot point on the profile image. The pivot point may be any point the user determines to need adjustment such as the low points on the graphs 404 and 410 of FIG. 4A. The user may then enter an amount of rotation in the Horizontal and Vertical text boxes 680, 682. Alternatively, the user may use the arrows 684 to incrementally change the tilt adjustment.

Figures 10A, 10B:
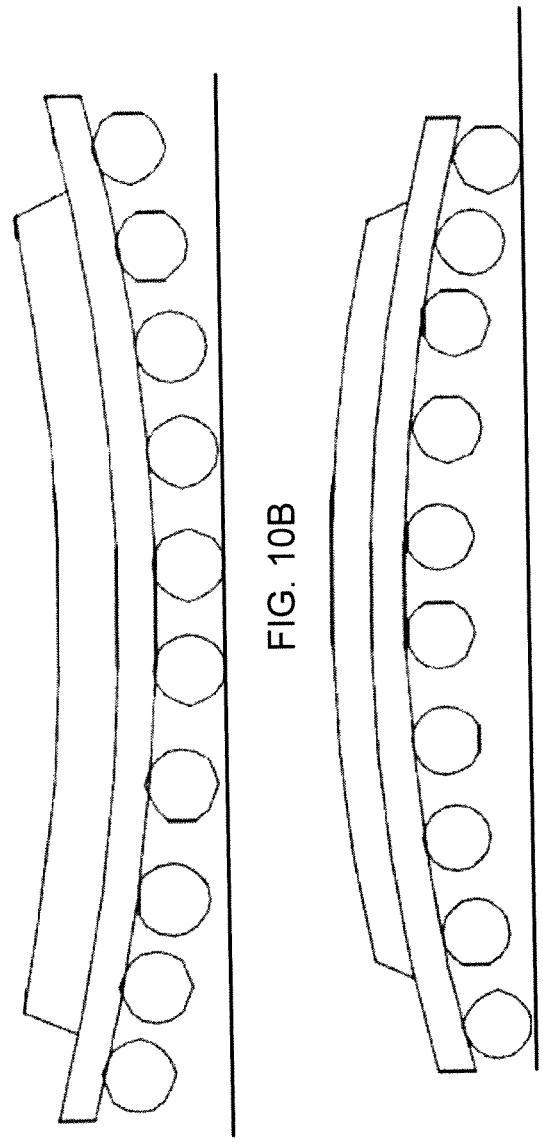
FIGS. 10A and 10B is an illustration of excessive warpage of a part.

A profile image may be useful in detecting, among other things, warpage in a part. As illustrated in FIG. 10A and FIG. 10B, excessive warpage of a part may result in weak or even failed soldering of bonds to a substrate or circuit board. A severely convex part, as shown in FIG. 10A may have ends that weak of no contact with the bonding surface of a substrate. Additionally, FIG. 10B illustrates a severely concave part. In this case, the bonds in the middle of the part may have weak or no contact with the bonding surface of a substrate.

A user may choose to manually check for warpage by selecting two points on a profile image to calculate a deviation in height between the two points. If the deviation is out of an acceptable range, the user may choose to discard the part. Warpage may also be automatically checked during an acoustic surface scan. The user may select, before performing a scan, to gather the maximum and minimum height of a part or of a portion of the part during an acoustic surface scan. The user may also define a tolerance in which parts with a difference between the maximum and minimum above the tolerance may be discarded. After an acoustic surface scan of a part, the system will automatically display to the user the maximum and minimum height, the deviation, and a recommendation to accept or reject the part based on either a user defined tolerance level or a built in tolerance level.

Figure 11:
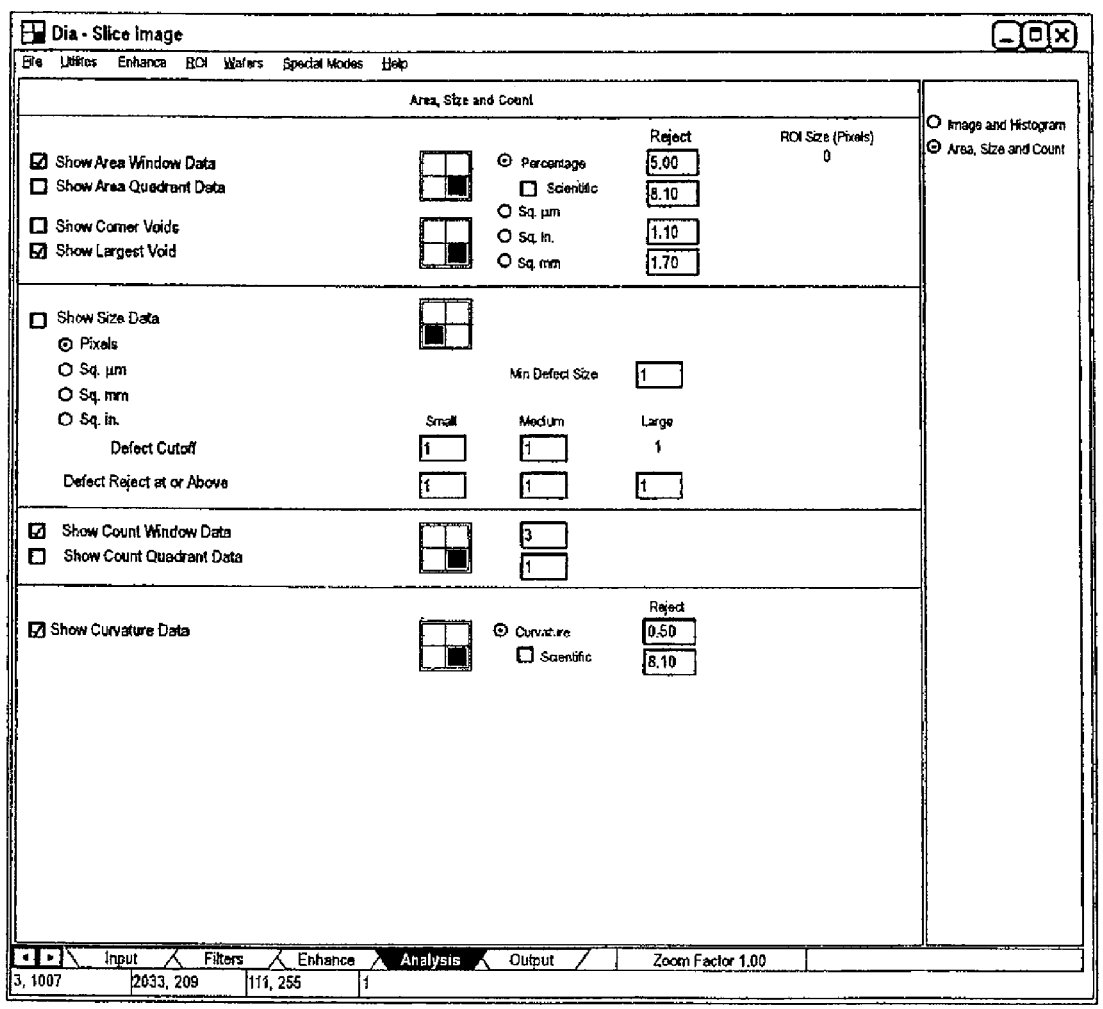
FIG. 11 illustrates a graphical user interface allowing a user to specify warpage information.

FIG. 11 is a screen shot which shows a graphical user interface that allows a user to enter data, such as maximum warpage, into the system. If the curvature of a part is out of an acceptable range, then the part can be rejected. This can be accomplished by, for example, a visual indication being given to an operator to put the faulty part into a reject bin or an indication to accept the part. Alternatively, the part reject process can be controlled by means of a robot.

FIG. 12 is a flowchart that shows program steps that are followed to allow the scanning acoustic microscope shown in FIG. 2 to generate acoustic profile data. At step 700 the system is initiated to begin an acoustic surface image scan. At step 702, the system places the transducer at a position corresponding to the position of the pixel to be scanned. At step 704, a pixel trigger is generated to start the pixel acquisition sequence. At step 706, the Pulser creates an acoustic pulse. Concurrently, at step 708 the waveform acquisition is initialized. As the waveforms are received the waveform data is stored in memory of the computing device as shown in FIG. 2. The storage of data may occur continuously, buffered by a line, bus or some other similar means. At step 710, the surface reflection echo is received. At step 712 the waveform acquisition ends. The waveform acquisition is then reset and ready for the next pixel trigger corresponding to the next pixel to be scanned. At step 714, the surface echo TOF is determined relative to the pixel trigger set by the user. At step 716, the surface echo time value is stored in the Image Data. At step 718 the image data is displayed on the image display monitor as it is acquired. At step 720 the system checks if all pixels have been acquired. If all pixels have not been acquired the system proceeds back to step 702 where the next pixel position will be scanned. This process is performed until all pixels have been acquired.

After all pixels have been acquired, the system proceeds to step 722 where the raster scan ends. The system then checks, at step 724, if the user has enabled the surface curvature measurement. If the surface curvature measurement is not enabled the scan is completed. If the surface curvature measurement is enabled, then at step 726 the surface curvature is calculated using the acoustic surface data collected. The curvature may be defined along a vertical and a horizontal line across the part being scanned or along any other user definable lines as described with reference to FIG. 4A and FIG. 8 above. As also described above, the curvature may also be calculated between two user definable points of an average curvature may be calculated. The results may be displayed on the Image Display Monitor, printed, or saved in memory as shown in FIG. 2. At step 728, the system checks if the surface curvature accept and reject thresholds have been enabled. If the threshold is not been enabled then the raster scan will end. If the threshold is enabled then at step 730 the upper and lower bounds which may be defined by the user is retrieved. At step 732, the part is checked if the surface curvature is within the limits set by the user. If the surface curvature is outside of the acceptable range, then at step 734 the monitor may display a reject indicator and the raster scan will end. If the surface curvature is within the acceptable range, then at step 736 the monitor will display an accept indicator.

One aspect of the present invention is a new capability for acoustic microscopes such as, for example, C-SAM® acoustic microscopes. In accordance with this aspect of the invention, the external surface topography of a device can be revealed, if desired, at the same time as its internal features or by itself. The acoustic surface profile software module can be used, for example, to measure warpage of plastic integrated circuits, flip chips, substrates, circuit boards, etc., without any sample preparation. The module can be loaded onto an existing microscope or can be incorporated into a new microscope.

In addition to causing bonding issues, warpage, at the surface of a part is often associated with internal problems such as cracks and delamination that can cause electrical failures. For example, the surface profile of a plastic encapsulated IC may show warpage in one quadrant. Internally, the same quadrant may reveal lead-frame delaminations. Having both images makes it easier, for example, to identify the processes that are causing the problem.

One advantage of the acoustic surface profile module is that it displays both the surface profile and the internal features on a single instrument, eliminating the need to buy a second instrument, and requires no additional scanning time, as the profile data is taken at the same time as the acoustic image data.

Figure 12A:
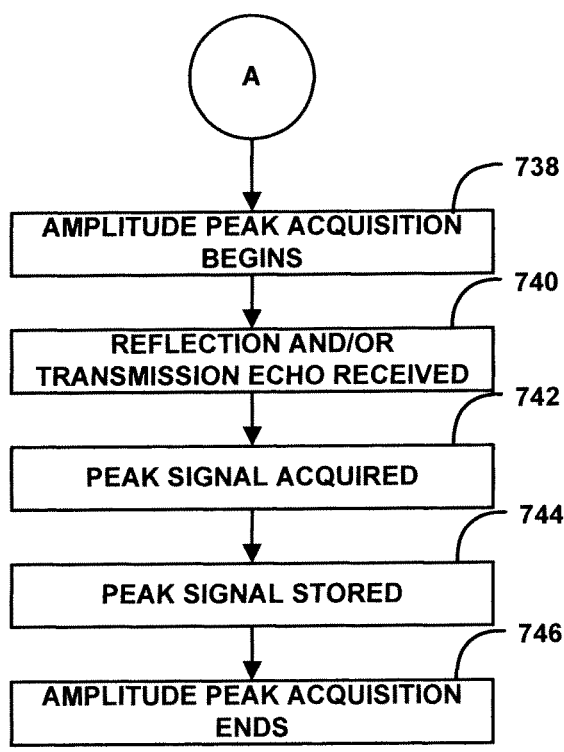
FIG. 12A is a flow chart used in conjunction with FIG. 12 to allow a scanning acoustic microscope to simultaneously collect internal and profile acoustic information.

FIG. 12A is a flowchart that shows program steps that are followed to allow the scanning acoustic microscope shown in FIG. 2 to simultaneously generate acoustic profile data while simultaneously generating data regarding internal acoustic impedance features. The steps of generating acoustic profile data along with the checking of the surface curvature are identical to the steps described in FIG. 12 above. Thus, the steps of FIG. 12 are incorporated herein. While the pulser is creates an acoustic pulse at step 706 in FIG. 12, at step 738, amplitude peak acquisition begins. At step 740, either one or both the reflection echo and the transmitted echo are received depending on the user settings. For example, a void in a part may have a strong reflection but no transmission. A user may choose to detect either a reflection or a transmission or try and detect both to give a more positive internal image. At step 743 the system checks one or both of the received echoes and selects a peak signal located within the user defined gate. The peak signal value gate is stored in the corresponding image data in step 744. At step 746 the peak amplitude acquisition ends and resets for the next trigger. The system then proceeds to step 718 as in FIG. 12 and displays the image data on the image display monitor. At step 720 the system checks if all pixels have been acquired. If all pixels have not been acquired then the system proceeds to block 702 in FIG. 12 where the next pixel location will be scanned.

One aspect of the invention concerns an acoustic micro imaging method that is useful in the inspection of a target. One step of the method is to scan the target with a focused pulsed acoustic beam, preferably in the ultrasonic range. The pulsed beam is sensed after it has been modified by interaction with the target, the modified pulsed beam being representative of acoustic impedance features inside of the target, as well as the surface topography of the target. A time-domain signal indicative of the modifications is generated, and then processed to produce a frequency domain representation of frequency selective modifications to the pulsed acoustic beam produced by said interaction with said target. The time-domain signal, the frequency domain signal representation and the surface topography data are displayed to provide two different visual indications of acoustic impedance features inside of the target together with surface topography data.

As described in greater detail in U.S. Pat. No. 6,890,302, surface and internal acoustic data collected may be subjected to a frequency domain conversion, preferably a Fourier transform, fast Fourier transform, discrete Fourier transform, of other such well known signal processing techniques.

Figure 13A:
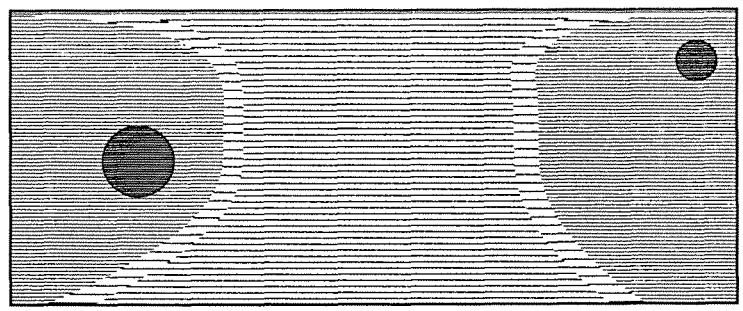
FIG. 13A-13C is an illustration of a profile image, time domain image, and frequency domain image capable of being displayed simultaneously.
Figure 13B:
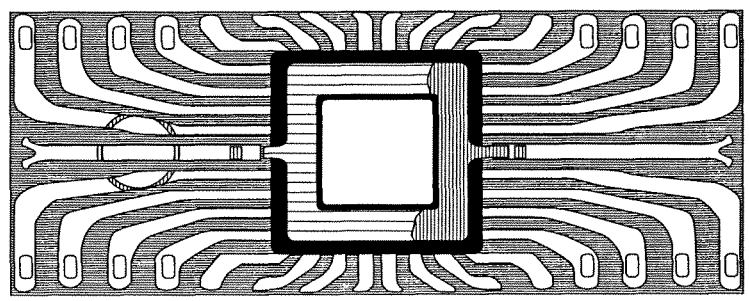
Figure 13C:
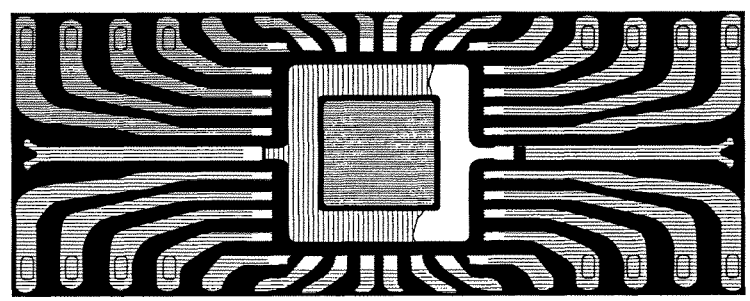

FIG. 13A shows a color coded surface topography of an IC similar to the surface profile image of FIG. 4A. FIG. 13B shows a time domain image of the IC. FIG. 13C shows a frequency domain representation of the IC. Displaying any combination of the images of FIG. 13A-13C may provide a user a better understanding of how defects on any one of the three views may affect the others.

Figure 14:
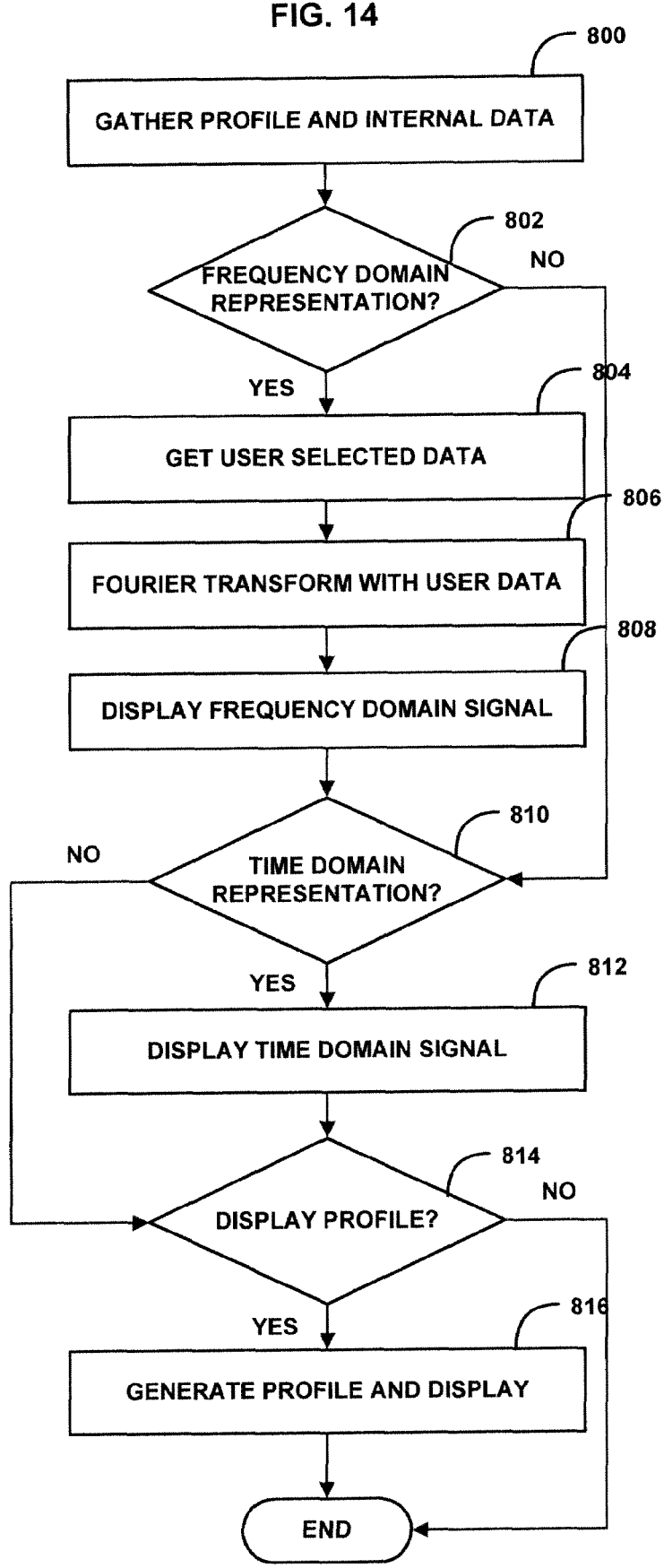
FIG. 14 is a flow chart illustrating how a user can cause visual indication of surface profile data to be simultaneously displayed with a time domain signal representation and/or a frequency domain signal representation.

FIG. 14 is a flowchart that illustrates how a user can cause a visual indication of surface profile data to be simultaneously displayed with, for example, a time domain signal representing internal acoustic impedance features, and/or a frequency domain representation. It should be understood that any combination of these three visual representations can be generated and displayed while the data is being generated. Alternatively, any combination of these three signals can be displayed by operation with a "virtual sample" of previously obtained data about a part.

At step 800 profile and internal data may be collected as described above. At step 802, the system checks whether the user has selected the frequency domain representation to be displayed. If the frequency domain representation is not selected to be displayed the system proceeds to step 810. If the frequency domain representation is selected to be displayed, then at step 804 the computer collects the user selected data. The user selected data of step 804 refers to the frequency related characteristics or ranges in which a user is interested in analyzing a part. For example, a user may be interested in seeing a visual indication of how a part looks with respect to a particular band of frequencies. To accomplish this, the user selected data (e.g., a band of frequencies) is input into the system, which then applies a Fourier transfer at step 806 using the frequency data on a time domain signal. The resulting transformed signal is then displayed at step 808 on a display either by itself or in combination with a time domain signal and a surface topography image if the time domain representation is selected by the user at step 810.

At step 810, if the time domain representation is not selected to be displayed, the system proceeds to step 814. If the time domain representation is selected to be displayed then at step 812 the resulting time domain representation is displayed either by itself or in combination with the frequency domain representation and/or the surface topography image.

At step 814 if the surface topography is not selected to be displayed the process ends. If the surface topography is selected to be displayed then at step 816 the surface topography image may be displayed in combination with either or both of the frequency domain representation of the time domain signal representation.

While the present invention has been described with reference to specific examples, which are intended to be illustrative only and not to be limiting of the invention, it will be apparent to those of ordinary skill in the art that changes, additions or deletions in addition to those explicitly described above may be made to the disclosed embodiments without departing from the spirit and scope of the invention.

What is claimed is:

1. A scanning acoustic microscope, comprising:
an ultrasonic transducer;
a data storage memory;
a display;
a scanner assembly driven by a motor on which the ultrasonic transducer is mounted;
a controller that is electrically connected to the transducer, the data storage memory, this display and the motor, the controller being adapted to
cause the motor to move the transducer along a path with respect to a sample,
cause the ultrasonic transducer to emit at least one pulse of acoustic energy towards the sample at each point in a plurality of points along the path,
cause the ultrasonic transducer to receive a set of reflection signals that correspond to each one of the at least one pulses emitted therefrom,
cause each set of reflection signals to be stored in the data storage memory,
use at least some of the sets of reflection signals stored in the memory to generate an image of a profile of the sample that is then shown on the display, and
use the same at least some of the sets of reflection signals to generate an image that is representative of acoustic impedance features in the interior of the sample and that is shown on the display simultaneously with the profile image; and
wherein the image of the profile of the sample shows a variation in height along a line across a surface of the sample in which the variation in height is in reference to a zero point, and the image of the profile includes a color-coded indication of the topography of the surface of the sample.

2. The scanning acoustic microscope of claim 1, wherein the motor assembly comprises a balanced linear motor assembly that includes a rotor on which the transducer is mounted, a stator on which the rotor and transducer are mounted for movement along a first linear path defined by the stator, and a counterweight that is mounted for movement along a second linear path that is parallel to the first linear path, the counterweight having a mass that is generally equal to the mass of the rotor and the transducer.

3. The scanning acoustic microscope of claim 2, wherein the counterweight is adapted to be moved, when the sample is being interrogated, along the second linear path at the same time that the rotor and transducer are being moved along the first linear path.

4. The scanning acoustic microscope of claim 2, further comprising a second linear motor assembly for moving at least the transducer in a direction that is perpendicular to the first linear path.

5. The scanning acoustic microscope of claim 2, further comprising a second balanced motor assembly for moving at least the transducer in a direction that is perpendicular to the first linear path.

6. The scanning acoustic microscope of claim 2, wherein the first linear path is co-linear with the second linear path.

7. The scanning acoustic microscope of claim 2, wherein the counterweight comprises a second ultrasonic transducer.

8. The scanning acoustic microscope of claim 2, wherein the transducer can be returned to a selected speed of the balanced linear motor assembly with changing directions without inducing vibration.

9. The scanning acoustic microscope of claim 2, further comprising a belt and pulley assembly that connects the counterweight to the transducer and rotor.

10. The scanning acoustic microscope of claim 3, wherein the first and second linear paths are spaced apart from each other, the center of the mass of the counterweight being located to reduce at least some of the rotational forces that are generated when the transducer is slowed down and changes direction.

11. The scanning acoustic microscope of claim 1, wherein the transducer follows one or more non-linear traces when the sample is being interrogated.

12. The scanning acoustic microscope of claim 1, wherein the transducer is operatively coupled to the sample via a coupling medium when the sample is being interrogated, the controller is being adapted to cause the ultrasonic transducer to emit a pulse of acoustic energy toward each on of the plurality of three-dimensionally varied points located within a given volume defined inside of the sample, transducer having, for each one of the pulses, a focal point that is disposed at the same location within the given volume of the sample as the corresponding one of the three dimensionally varied points.

13. The scanning acoustic microscope of claim 1, wherein the transducer is operatively coupled to the sample via a coupling medium when the sample is being interrogated, the controller being adapted to cause the ultrasonic transducer to emit a pulse of acoustic energy toward each one of a plurality of three-dimensionally varied points, located within a given volume defined inside of the sample, the transducer having, for each one of the pulses, a focal point that is disposed at the same location within the given volume of the sample as the corresponding one of the three dimensionally varied points, the controller being further adapted to cause the transducer to receive a reflection signal corresponding to each one of the pulses, each one of the reflection signals comprising an A-Scan of the sample that is in-focus at the point within the given volume of the sample corresponding thereto, all of the reflection signals representing acoustic impedance features present within the given volume defined inside of the sample.

14. The scanning acoustic microscope of claim 1, wherein the sample comprises a microelectronic sample.

15. The scanning acoustic microscope of claim 1, wherein controller is adapted to cause the transducer to be moved in an X-Y raster scan with respect to the sample.

16. The scanning acoustic microscope of claim 1, wherein the sample comprises a sealed package.

17. The scanning acoustic microscope of claim 1, wherein the sample comprises a biological material.

18. The scanning acoustic microscope of claim 1, wherein the acoustic impedance feature image is generated from time-domain signals.

19. The scanning acoustic microscope of claim 18, wherein the controller is adapted to process the time-domain signals to produce frequency domain representations of frequency selective modifications to the pulses of acoustic energy that are produced by interaction with the sample.

20. The scanning acoustic microscope of claim 1, wherein the sample comprises a ceramic or metal plate.

21. The scanning acoustic microscope of claim 1, wherein the controller uses all off the sets of reflection signals stored in the memory to generate the profile image.

22. The scanning acoustic microscope of claim 1, wherein the controller uses all off the sets of reflection signals stored in the memory to generate the interior acoustic impedance feature image.

* * * * *